(12) United States Patent
Potyrailo et al.

(10) Patent No.: US 9,045,973 B2
(45) Date of Patent: Jun. 2, 2015

(54) SYSTEM AND METHOD FOR MONITORING DOWN-HOLE FLUIDS

(75) Inventors: Radislav Alexandrovich Potyrailo, Niskayuna, NY (US); Cheryl Margaret Surman, Albany, NY (US); Nicholas Josep Ellson, Bristol (GB)

(73) Assignee: General Electric Company, Niskayuna, NY (US)

( * ) Notice: Subject to any disclaimer, the term of this patent is extended or adjusted under 35 U.S.C. 154(b) by 703 days.

(21) Appl. No.: 13/331,003

(22) Filed: Dec. 20, 2011

(65) Prior Publication Data
US 2013/0154847 A1   Jun. 20, 2013

(51) Int. Cl.
*H04B 5/00*   (2006.01)
*E21B 47/10*   (2012.01)

(52) U.S. Cl.
CPC .............. *E21B 47/10* (2013.01); *H04B 5/0043* (2013.01)

(58) Field of Classification Search
CPC .......................... H04B 5/0043; G06K 19/0717
USPC ....................................................... 340/856.4
See application file for complete search history.

(56) References Cited

U.S. PATENT DOCUMENTS

| | | | |
|---|---|---|---|
| 7,031,560 B2 | 4/2006 | Lelong-Feneyrou et al. | |
| 7,038,470 B1 * | 5/2006 | Johnson | 324/664 |
| 7,911,345 B2 | 3/2011 | Potyrailo et al. | |
| 8,342,242 B2 * | 1/2013 | Roddy et al. | 166/255.1 |
| 8,736,425 B2 * | 5/2014 | Potyrailo | 340/10.3 |
| 2007/0084277 A1 | 4/2007 | Steinsiek | |
| 2007/0090927 A1 | 4/2007 | Potyrailo et al. | |
| 2007/0131418 A1 | 6/2007 | Barrow et al. | |
| 2008/0236814 A1 | 10/2008 | Roddy | |
| 2010/0059221 A1 | 3/2010 | Vannuffelen et al. | |

FOREIGN PATENT DOCUMENTS

| | | |
|---|---|---|
| GB | 2460668 A | 9/2009 |
| WO | 0173380 A1 | 10/2001 |

OTHER PUBLICATIONS

PCT Search Report and Written Opinion dated Jan. 27, 2014 from corresponding Application No. PCT/ US2012/070448.
Co-pending U.S Appl. No. 12/977,599, filed on Dec. 23, 2010, entitled Temperature-Independent Chemical and Biological Sensors.
Janata, "Electrochemical Sensors and Their Impedances: A Tutorial", Critical Reviews in Analytical Chemistry, vol. 32, No. 2, pp. 109-120, 2002.
Pejcic et al., "Impedance Spectroscopy: Over 35 Years of Electrochemical Sensor Optimization", Electrochimica Acta, vol. 51, pp. 6217-6229, 2006.

(Continued)

*Primary Examiner* — Albert Wong
(74) *Attorney, Agent, or Firm* — Andrew J. Caruso (57) ABSTRACT

In one aspect the present invention provides a down-hole monitoring system, comprising one or more pieces of down-hole equipment, for example a down-hole logging tool, and at least one resonant sensor for obtaining physical and chemical parameters of a down-hole fluid in proximity to the sensor. In another aspect, the present invention provides a method for detecting material properties of a down-hole fluid, the method comprising placing a resonant LCR sensor within a piece of down-hole equipment, taking sensor readings down-hole, transmitting the sensor readings to a reader device, and analyzing the sensor readings.

22 Claims, 8 Drawing Sheets

(56) References Cited

OTHER PUBLICATIONS

Josee et al., "AC-Impedance-Based Chemical Sensors for Organic Solvent Vapors", Sensors and Actuators B, vols. 35-36, pp. 363-369, 1996.

Amrani et al., "Multi-Frequency Measurements of Organic Conducting Polymers for Sensing of Gases and Vapours", Sensors and Actuators B, vol. 33, pp. 137-141, 1996.

Yang et al., "Chemical Identification Using an Impedance Sensor Based on Dispersive Charge Transport", Applied Physics letters, vol. 88, pp. 074104-1 to 074104-3, 2006.

Amrani et al., "Multi-Frequency Interrogation Technique Applied to Conducting Polymer Gas and Odour Sensors", IEE Proc.—Set. Meas. Technol., vol. 146, No. 2, pp. 95-101, 1999.

Chuang et al., "Embeddable Wireless Strain Sensor Based on Resonant rf Cavities", Review of Scientific Instruments, vol. 76, pp. 094703-1 to 094703-7, 2005.

Bauer et al., "Resonant Nanocluster Technology—From Optical Coding and High Quality Security Features to Biochips", Nanotechnology, vol. 14, pp. 1289-1311, 2003.

Haes et al., "A Nanoscale Optical Biosensor: Sensitivity and Selectivity of an Approach Based on the Localized Surface Plasmon Resonance Spectroscopy of Triangular Silver Nanoparticles", J. Am. Chem. Soc., vol. 124, pp. 10596-10604, 2002.

Grimes et al., "Wireless Magnetoelastic Resonance Sensors: A Critical Review", Sensors, vol. 2, pp. 294-313, 2002.

Homola et al., "Surface Plasmon Resonance Sensors: Review", Sensors and Actuators B, vol. 54, pp. 3-15, 1999.

Butler et al., "Wireless, Passive, Resonant-Circuit, Inductively Coupled, Inductive Strain Sensor", Sensors and Actuators A, vol. 102, pp. 61-66, 2002.

Lu et al., "MEMS-Based Inductively Coupled RFID Transponder for Implantable Wireless Sensor Applications", IEEE Transactions on Magnetics, vol. 43, No. 6, pp. 2412-2414, Jun. 2007.

Tanaka et al., "Quartz Crystal Capacitive Sensor With Inductance-Capacitance Resonance Circuit for Vapor Sensing", Japanese Journal of Applied Physics, vol. 46, No. 11, pp. 7509-7511, 2007.

Ong et al., "Design and Application of a Wireless, Passive, Resonant-Circuit Environmental Monitoring Sensor", Sensors and Actuators A, vol. 93, pp. 33-43, 2001.

Potyailo et al., "Multianalyte Chemical Identification and Quantitation Using a Single Radio Frequency Identification Sensor", Anal. Chem., vol. 79, pp. 45-51, 2007.

Barsoukov et al., Impedance Spectroscopy: Theory, Experiment, and Applications; Second Edition, pp. 205-264, 2005.

\* cited by examiner

SYSTEM AND METHOD FOR MONITORING DOWN-HOLE FLUIDS

The present invention relates generally to chemical, physical, and biological sensors, and more particularly, to highly selective thermally robust chemical, physical, and biological sensors for use in describing fluid characteristics down-hole.

BACKGROUND INFORMATION

The ability to accurately describe oil field reservoir fluids has positive benefits during both the exploration and production phases of a hydrocarbon-containing reservoir. During production, well-specific knowledge of the fluid composition being removed from the reservoir can yield valuable information for both reservoir modeling and management. It would be advantageous to discover sensor technology that can be permanently deployed within a well bore, and can be used to monitor changes in reservoir fluid characteristics over time. Such sensor technology could provide more accurate data for input into reservoir models without the need for disruptive individual well tests. The technology could also be deployed in production logging tools to perform down-hole fluid analysis on an automated basis.

Fluid analysis based on measurement of the fluid's various dielectric properties holds promise as a means for accurately determining both chemical (e.g. composition-related characteristics) and physical (e.g., viscosity, density, temperature, polarity) characteristics of a fluid. Such methodology could provide advantages over conventional analytical techniques such as optical spectroscopy, nuclear magnetic resonance spectroscopy, and resistivity, in that fluids such as down-hole fluids could be characterized in situ using sensors attached to one or more features associated with a hydrocarbon production well (e.g. a well logging tool). Down-hole fluid characteristics might be determined more efficiently and in greater detail by probing the various dielectric properties of the fluid in situ, rather than through the use of conventional analytical techniques which can require well sampling and remote analysis of the sampled fluids and be attended by significant delays in decision making based on analysis results. Fluid analysis based on measurement of a down-hole fluid's various dielectric properties can provide information on molecular composition of fluid components, hydrocarbon chain length of fluid components, the degree to which a hydrocarbon-containing fluid is saturated or unsaturated, and the polarity of the fluid among others. Because fluid analysis based on measurement of the fluid's various dielectric properties does not involve optical spectroscopy, sensor fouling is less problematic than in down-hole fluid monitoring systems involving optical probe techniques.

Traditionally, impedance spectroscopy, a known form of dielectric fluid analysis, has been applied to characterize fundamental aspects of materials performance. In impedance spectroscopy, a material is positioned between the electrodes of a sensor and is probed over a wide frequency range, from a fraction of a Hertz (Hz) to tens of gigahertz (GHz). While impedance spectroscopy is a useful tool in materials characterization, cell analysis, and particle sizing, its applicability in practical sensors for detection of trace levels of analytes is limited by low sensitivity in known measurement configurations and prohibitively long acquisition times over the broad frequency ranges involved.

Resonant sensors have proven useful in chemical, physical, and biological sensing applications. Resonant sensors based on inductor-capacitor-resistor (LCR) structures with multivariable analysis of the resonance spectra produced, have not been shown to be useful in down-hole environments so critical to hydrocarbon exploration and production activities.

Thus, there remains an unmet need in the areas of chemical, biological, and physical detection for sensors which may be employed in down-hole environments and which offer a combination of high sensitivity, favorable signal-to-noise ratio, high selectivity, high accuracy, and high data acquisition speeds.

BRIEF SUMMARY

In one embodiment, there is provided a down-hole system including down-hole equipment and at least one resonant sensor for obtaining physical and chemical parameters of a down-hole fluid.

In an alternate embodiment, there is provided a method for detecting material properties of a down-hole fluid comprising placing at least one resonant LCR sensor within down-hole equipment, taking sensor readings down-hole, transmitting the sensor readings to a reader device, and analyzing the sensor readings.

In yet another embodiment, there is provided down-hole fluid monitoring system comprising down-hole equipment; and at least one resonant LCR sensor comprising a sensing material.

The foregoing has outlined rather broadly the features of embodiments of the invention so that the detailed description of the invention that follows may be better understood. Additional features and advantages of the invention will be described hereinafter, which form the subject of the claims of the invention.

For a more complete understanding of the invention, and the advantages thereof, reference is now made to the following descriptions taken in conjunction with the accompanying drawings.

DETAILED DESCRIPTION OF THE INVENTION

Embodiments of the invention are directed to systems and methods for detection with high sensitivity, selectivity, accuracy, signal-to-noise, and data acquisition speed. Embodiments of the invention utilize the principle that individual chemicals and biological species will have different dielectric properties, that those properties will vary in response to temperature changes, and that those properties may be probed effectively in the context of a process fluid being removed from a fluid reservoir using a resonant sensor such as a resonant LCR sensor as the probe. According to embodiments of the invention, instead of using conventional impedance spectroscopy for scanning across a wide frequency range, from a fraction of a Hertz (Hz) to tens of gigahertz (GHz), a resonant inductor-capacitor-resistor (LCR) sensor may be used to rapidly acquire spectral data and with a high signal-to-noise ratio across a relatively narrow frequency range. Instead of measuring the broad impedance response of a material, embodiments of the present invention enhance the ability for sensing and characterizing a process fluid, by putting the sensing region in proximity to electrodes constituting a resonant circuit. Thus, dielectric, dimensional, charge transfer, and other properties of a process fluid may be detected by changes induced in the electronic properties of the resonant sensor circuit brought about by the proximity of the process fluid to the resonant sensor circuit.

Referring to the drawings in general, it will be understood that the illustrations are for the purpose of describing a particular embodiment of the invention and are not intended to limit the invention thereto.

Figure 1:
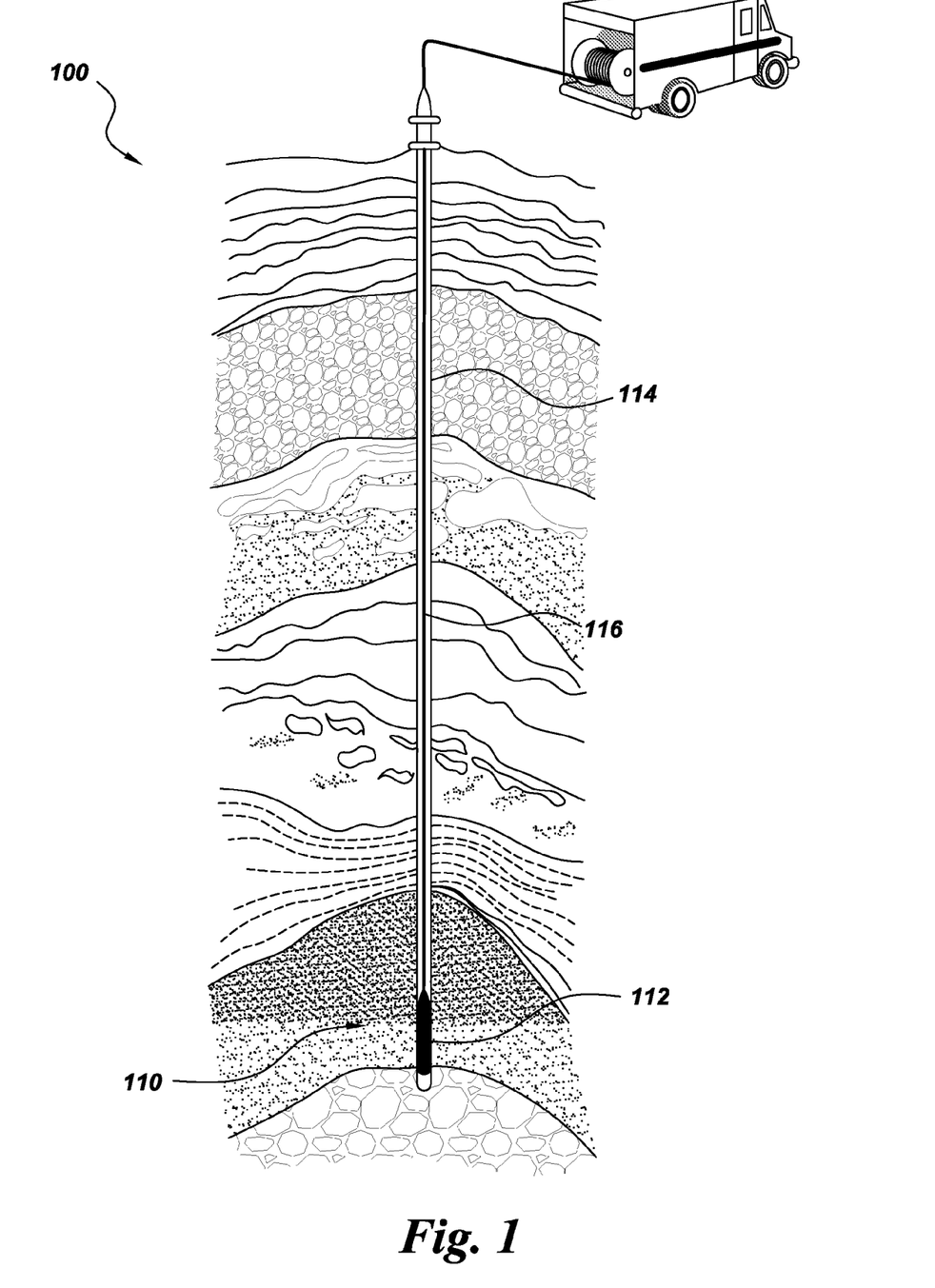
FIG. 1 is a schematic view illustrating a wireline logging assembly incorporating a sensing system in accordance with an embodiment of the invention.

Referring to FIG. 1 there is shown a sensing system 110 comprising at least one resonant sensor, for example a resonant LCR sensor, as part of a wireline logging assembly 100. Although shown implemented in a well on land, it should be appreciated that embodiments of the invention are also applicable to subsea wells offshore. Well logging, also known as borehole logging, is the practice of making a detailed record (a well log) of geological formations penetrated by a borehole. The log may be based either on visual inspection of samples brought to the surface (geological logs) or on physical measurements made by instruments lowered into the hole (geophysical logs). Wireline logs are a type of geophysical log.

Wireline logs are typically the product of detailed measurements of formation properties using electrically powered instruments to infer properties and make decisions about drilling and production operations. In wireline measurements, the logging tool 112 is lowered into the open well bore 114 on a wireline 116. Once lowered to the bottom of the interval of interest, measurements are taken as the sensor is being removed from the well bore. This is done in an attempt to maintain tension on the cable (which may have a tendency to stretch) as constant as possible for depth correlation and/or purposes. There is an exception to this practice where, in certain hostile environments, tool electronics might not survive the temperatures in the lower reaches of the well bore during the time required to lower the tool and then record measurements while pulling the tool up the well bore. Under such circumstances, "down log" measurements may be taken as the tool descends into the well bore, and then repeated as the logging tool is withdrawn of the well bore.

Most wireline measurements are recorded continuously as the logging tool moves through the well bore. However, certain fluid sampling and pressure-measuring tools require that the tool be stationary during measurements, increasing the chance that the tool or the wireline cable might become stuck at one or more points along the well bore.

Logging while drilling (LWD) tools take measurements in much the same way as wireline-logging tools, except that the measurements are taken by a self-contained tool near the bottom of the bottomhole assembly and are recorded downward (as the well is deepened) rather than upward from the bottom of the well bore.

Figure 2A:
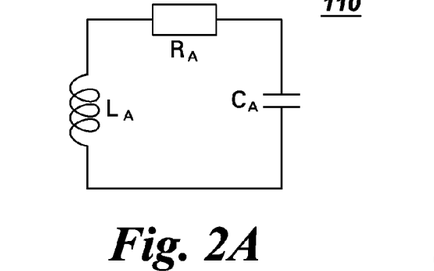
FIGS. 2A and 2B illustrate aspects of LCR sensors which may be used in accordance with one or more embodiments of the invention.

FIG. 2A illustrates a resonant LCR sensor component 108 (at times herein referred to simply as a resonant sensor) of a resonant sensor system 110. Such resonant sensors are characterized by an equivalent circuit comprising inductance $L_A$, capacitance $C_A$, and resistance $R_A$ components. Different environmental conditions such as conductivity, dielectric constant, and temperature of fluids in proximity to the sensor produce independent effects on the different components of the equivalent circuit. These independent effects may be correlated with the spectral features of the resonance impedance spectra and are resolved by the multivariable response of the sensor.

Resonant LCR sensor components 108 may be configured in a variety of ways. For example, the geometries of sensing elements of the sensor include coils, a plurality of electrodes, an interdigital electrode array, and other configurations known in the art.

In embodiments in which conductivity measurements of highly conducting fluids are desired, an inert protecting layer may be applied onto the sensor to separate the conducting medium from one or more resonant sensor sensing elements.

Typically, the $L_A$, $C_A$, and $R_A$ components of a resonant LCR sensor are made of electrically conductive materials disposed on a sensor substrate. Nonlimiting examples of conductive materials useful in the $L_A$, $C_A$, and $R_A$ components of a resonant LCR sensor include stainless steel, copper, silver, gold, platinum, aluminum, and other suitably conductive materials known in the art.

Nonlimiting examples of materials suitable for use as a resonant sensor substrate include dielectric materials, such as ceramics, glass, quartz, silicon, organic polymers, and other materials known in the art. In one embodiment, the resonant sensor substrate comprises the organic polymer poly (ethylene terephthalate).

In one or more embodiments, additional temperature-sensitive components are incorporated into the sensor equivalent circuit to facilitate and improve temperature effects. Nonlimiting examples of such additional temperature-sensitive components include capacitors, resistors, and integrated circuit memory chips. An integrated circuit memory chip may also store calibration and other parametric sensor data, and such data may be available before, during, and after sensor operation.

In one embodiment, the present invention provides for temperature-modulated spectral measurements of the sensor response. The temperature-modulated spectral measurements of the sensor response improve the accuracy and selectivity of sensor measurements of different fluids. This improvement originates from the temperature sensitivity of the complex permittivity ($\in'_r - j\in''_r$) of the monitored fluids and the correlation of the changes in the complex permittivity ($\in'_r - j\in''_r$) with changes in the resonant impedance spectrum of the sensor. The real part $\in'_r$ of the complex permittivity of the monitored fluid is also known as dielectric constant of the fluid. The imaginary part $\in''_r$ of the complex permittivity of the monitored fluid is directly proportional to the conductivity ($\sigma$) of the fluid. Table 1 illustrates nonlimiting examples of different temperature dependence of $\in'_r$ for different materials.

TABLE 1

| Material | Temperature Dependence of $\in'_r$ ($-100 \times d\in'_r/dT$ (° C.)) |
|---|---|
| dodecane | 0.12 |
| methane | 0.217 |
| Water | 36 |

Figure 3A:
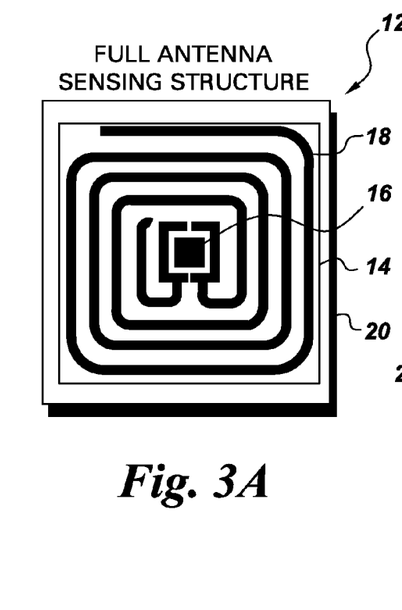
FIGS. 3A and 3B illustrate a full antenna sensing structure and a complimentary sensing structure, respectively, used according to one or more embodiments of the present invention.
Figure 3B:
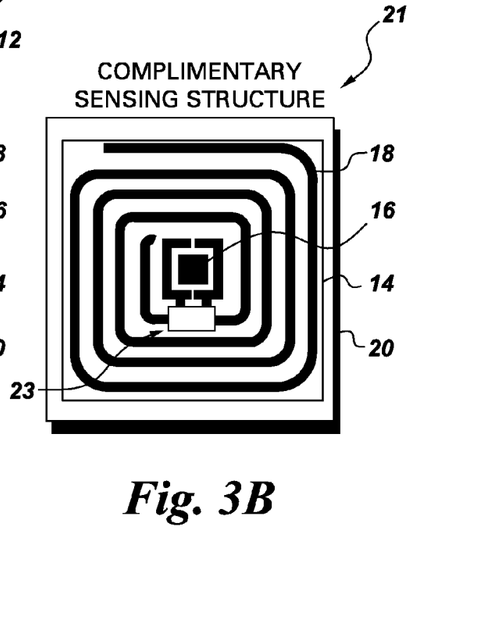

Two exemplary and nonlimiting embodiments of the sensor used in the sensing system 110 are shown in FIG. 3A and FIG. 3B. As illustrated in FIG. 3A, the sensing system 110 includes a sensor 12, which is a resonant circuit that includes an inductor-capacitor-resistor sensor (LCR). The LCR sensor comprises at least three temperature-dependent coefficients related to the inductance L, capacitance C, and resistance R properties of the LCR circuit. Each of the at least three temperature-dependent response coefficients of the LCR circuit are at least 5 percent different from one another.

The sensor antenna 18 comprises electrodes disposed on a substrate (at times herein referred to as the sensor substrate), and further, the antenna constitutes the resonant circuit of the sensor. In some embodiments a sensing material 14 is applied onto the resonant circuit. By applying the sensing material 14 onto the resonant circuit, the impedance response of the circuit will be altered. The sensor 12 may be a wired sensor or a wireless sensor. The sensor 12 may also include a memory chip 16 coupled to resonant antenna 18 which itself is coupled to a substrate 20. The memory chip 16 may include manufacturing, user, calibration and/or other data stored thereon. The memory chip 16 may be an integrated circuit (IC) device and it may include RF signal modulation circuitry fabricated using a complementary metal-oxide semiconductor (CMOS) process and a non-volatile memory. The RF signal modulation circuitry components include a diode rectifier, a power supply voltage control, a modulator, a demodulator, a clock generator, and optionally, other components. In one embodiment, the resonant sensor used comprises one or more sensor electrodes in contact with the sensor substrate wherein the sensor substrate and sensor electrodes have substantially different temperature response coefficients.

FIG. 3B illustrates an alternative embodiment of the sensor 12, designated by reference numeral 21, wherein a complementary sensor 23 comprising the sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Non-limiting examples of complementary sensors are interdigitated sensors, resistive sensors, and capacitive sensors. The resonant sensors shown in FIG. 3A and FIG. 3B may be employed for detection of individual chemical and biological species, and may be used to monitor a wide variety of chemical and physical parameters of fluids encountered in down-hole environments.

Further details on the use and constitution of sensors such as 12 and 21 may be found in U.S. patent application Ser. No. 12/977,599, filed Dec. 23, 2010, which is incorporated in its entirety herein by reference. A discussion of complementary sensors is described in U.S. Pat. No. 7,911,345, which is incorporated herein by reference.

Figure 2B:
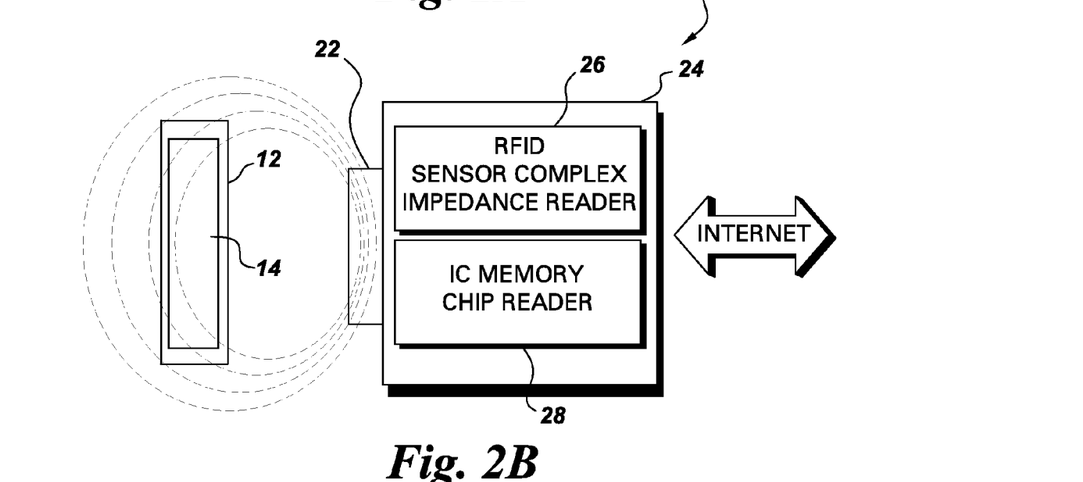
Figure 4A:
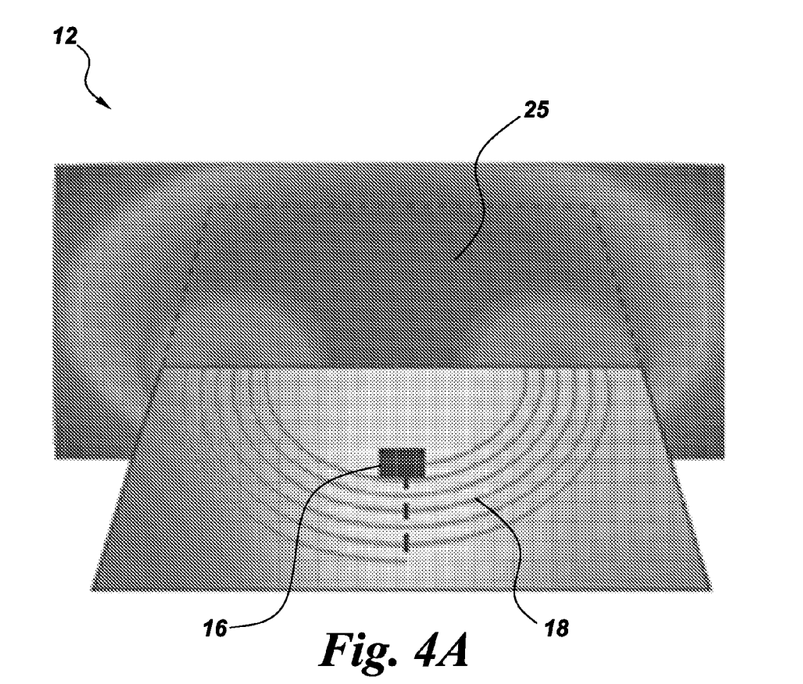
FIG. 4A schematically illustrates an electromagnetic field associated with the sensors of FIGS. 3A and 3B.

In one embodiment, a RFID tag (e.g. a 13.56 MHz RFID tag) may be employed as illustrated in FIG. 4A. During operation of a sensing system 110, the impedance Z(f) of the sensor antenna 18 and the digital sensor calibration parameters stored on the memory chip 16 may be acquired. Measurement of the resonance impedance Z(f) of the antenna 18 and the reading/writing of digital data from the memory chip 16 are performed via mutual inductance coupling between the RFID sensor antenna 18 and a pickup coil 22 (FIG. 2B) of a reader 24 (FIG. 2B) or via direct wiring. In one embodiment, the present invention provides a down-hole monitoring system comprising resonant LCR sensor comprises a memory chip operable at one or more of a plurality of predetermined frequency ranges, forming a RFID sensor. In one embodiment, the RFID sensor operates within a frequency range of from 1 kHz to 50,000 GHz. In another embodiment, the RFID sensor operates within a frequency range of from 5 kHz to 500 GHz. In yet another embodiment, the RFID sensor operates within a frequency range of from 10 kHz to 50 GHz. In one embodiment, the RFID sensor operates at a frequency of a 125 kHz, a frequency of 134 kHz, or a frequency of 13.5 MHz.

Figure 4B:
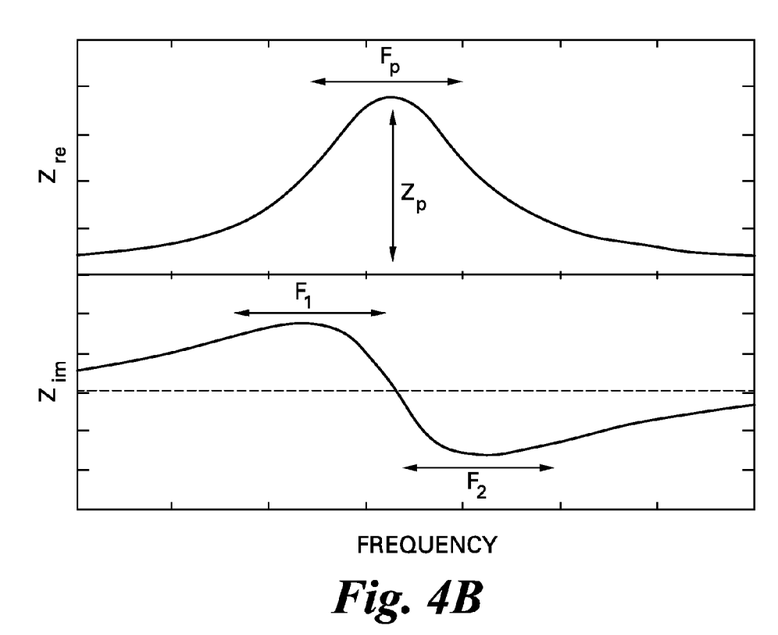
FIG. 4B schematically represents two parameters of the real part of the impedance and two parameters of the imaginary part of the impedance of a sensor in accordance with one or more embodiments of the invention.

The origins of response of a resonant impedance sensor, such as the sensors shown in FIG. 3A and FIG. 3B, to parameters of interest are further illustrated in FIG. 4A and FIG. 4B. The electromagnetic field 25 generated by a resonant impedance sensor system 110, such as that shown in FIG. 2B, emanates from the plane of the sensor antenna 18 and into the surrounding down-hole environment where the electromagnetic field interacts with fluid present in the surrounding down-hole environment. The nature and amount of energy transfer from the sensor to the fluid is dependent upon the dielectric properties of the fluid. Energy transfer from the resonant impedance sensor to the fluid in the surrounding environment alters the characteristics of the electromagnetic field produced by the sensor and such changes in the characteristics of the electromagnetic field produced by the sensor can be correlated with one or more properties of the fluid. Thus, one or more biological, chemical and/or physical parameters of the fluid may be probed in a down-hole environment using one or more embodiments of the present invention. When the down-hole environment is relatively conductive, a protecting layer 14 may be included in the sensor system to separate the conducting medium in the surrounding down-hole environment from the resonant antenna 18. In one embodiment, the characteristics of relatively conducting species (liquids or solids) present in the down-hole environment can be performed using one or more embodiments provided by the present invention.

In one embodiment, a resonant impedance sensor system comprising sensor 12 comprises a pickup coil 22 and is used to determine one or more parameters of a fluid in proximity to the sensor in a down-hole environment. In another embodiment, a resonant impedance sensor system comprising sensor 12 comprises a galvanically coupled reader and is used to determine one or more parameters of a fluid in proximity to the sensor in a down-hole environment. In an alternate set of embodiments, a resonant impedance sensor system 110 comprising sensor 21 comprises a pickup coil 22 and/or a galvanically coupled reader and is used to determine one or more parameters of a fluid in proximity to the sensor in a down-hole environment. In one embodiment, the reader is configured to read signals through a frequency sweep. In another embodiment, the reader is configured to read signals through a time-resolved sweep. In yet another embodiment, the reader is configured to read signals through a ring-down detection.

In one embodiment, a down-hole monitoring system comprises one or more pieces of equipment (e.g. a logging tool, a drill unit, a drilling fluid delivery unit, or an optical sensing unit) and a resonant sensor 21 (FIG. 3B) configured to monitor physical and chemical parameters of a down-hole fluid in proximity to the equipment being used in the well bore. In one embodiment, sensing is performed by monitoring the changes in the properties of the sensing material 14 as probed by characteristics of an electromagnetic field 25 sensed by complementary sensor 23. In one embodiment, the sensor provides a response to a temperature of a down-hole fluid in proximity to the sensor, wherein the response to the temperature is substantially independent of a response by the sensor to one or more chemical characteristics of the down-hole fluid in proximity to the sensor.

As noted, in systems providing measurements in highly conducting down-hole fluids employing a resonant sensor such as 12 or 21, a protective layer 14 separating the antenna 18 from the down-hole environment prevents the sensor from electrical shorting and loss of sensor resonance. Typically, the protective layer 14 is disposed on the antenna 18 and is at times herein referred to as a sensing film or a sensing material. The response of such resonant impedance sensors to chemical and/or biological parameters of a down-hole fluid depends upon changes in the dielectric properties of the down-hole fluid, and/or upon changes in the dielectric and dimensional properties of the sensing film separating the antenna of the sensor from the down-hole fluid resulting from contact between the sensing film and the down-hole fluid. As will be appreciated by those of ordinary skill in the art, contact between the sensing film and the down-hole fluid may alter either or both the dielectric and dimensional properties of the sensing film. An appropriate sensing film may be selected based upon the sensitivity of film dielectric and/or dimensional properties to one or more analytes sought to be detected in the down-hole fluid. A variety of suitable analyte-specific and/or analyte-selective sensing films are known to those of ordinary skill in the art. In one embodiment, analyte-induced changes in the sensing film are detected as changes in the impedance of the resonant impedance sensor circuit brought about by changes in sensing film resistance and capacitance in the film regions between the coil turns of the sensor antenna 18. Such changes can be relied upon to provide a high level of diversity of response of an individual resonant impedance sensor to various down-hole environments. In this sense, the present invention creates an opportunity to replace multiple conventional sensors used to measure the characteristics of a down-hole fluid with a single resonant impedance sensor.

Referring to FIGS. 4A and 4B, the electromagnetic field 25 generated in the sensor extends out from the plane of the sensor antenna 18 (FIG. 4A). The electromagnetic field 25 is affected by changes in the dielectric properties of one or more materials in proximity to the sensor as energy is transferred from the sensor to one or more constituents of the down-hole environment, for example a down-hole fluid comprising water and methane. In one embodiment, changes in the complex impedance parameters (e.g. Fp, Zp, F1, and F2 (FIG. 4B)) of a resonant impedance sensor circuit (e.g. antenna 18) may be monitored. Complex impedance parameters are illustrated by FIG. 4B and include Fp, the frequency of the real part of the complex impedance, and Zp, the magnitude of the real part of the complex impedance. F1 and F2 are, respectively, the resonant and anti-resonant frequencies of the imaginary part of the complex impedance. By applying Principal Components Analysis (PCA) to either the entire impedance spectrum or multiple selected features, such as Fp, F1, F2, Zp, etc., interferences are rejected with a single sensor. As will be appreciated by those of ordinary skill in the art, Principal Components Analysis is a nonlimiting example of multivariate analytical techniques available for analysis of spectral features of the sensor response. Other examples of multivariate analytical techniques available for this purpose include Independent Component Analysis (PCA), Linear Discriminant Analysis (LDA), and Flexible Discriminant Analysis (FDA).

In one embodiment, the sensing system 110 is configured for use in sample cell. Comparison can be made to similarly configured systems not comprising a resonant sensor, and comprising instead a non-resonant electrode based sensor capable of probing the dielectric properties of a fluid contained within the cell. The effects of changes in the dielectric constant of a sample fluid in the cell on the two types of sensors have been compared, and the results of these comparisons highlight some of the advantages attending various embodiments of present invention. Fluids of different dielectric constant are introduced into the sample cell configured either with a resonant sensor or a non-resonant electrode based sensor, and the impedance response of the sensor is monitored. Comparison of the sensing performance of the resonant sensor and non-resonant electrode sensor can then be accomplished. In such comparisons, a signal-to-noise ratio (SNR) and a detection limit (DL) from two sensor types can be ascertained.

For selective analyte quantitation using individual resonance-enhanced multivariable sensors, complex impedance spectra of the resonant sensors are measured as shown in FIG. 4B. Several parameters from the measured real and imaginary portions of the impedance may be calculated from the sensor measurements. Examples of calculated parameters include the frequency of the maximum of the real part of the impedance ($F_p$), the magnitude of the real part of the impedance ($Z_p$), the resonant frequency of the imaginary part of the impedance ($F_1$), and the anti-resonant frequency of the imaginary part of the impedance ($F_2$). Additional parameters can also be calculated (e.g. the zero-reactance frequency, and the quality factor). However, the use of $F_p$, $F_1$, $F_2$, and $Z_p$ has been found adequate for selective sensing. Varying the temperatures at which the measurements are carried out by, for example, varying the temperature of the fluids the dielectric properties of which are being probed, the sensor may respond differently to each analyte and/or interferences sensed. By applying multivariate analysis of the full impedance spectrum or the parameters calculated therefrom, quantitation of analytes and rejection of interferences may be performed using individual sensors.

Figure 5A:
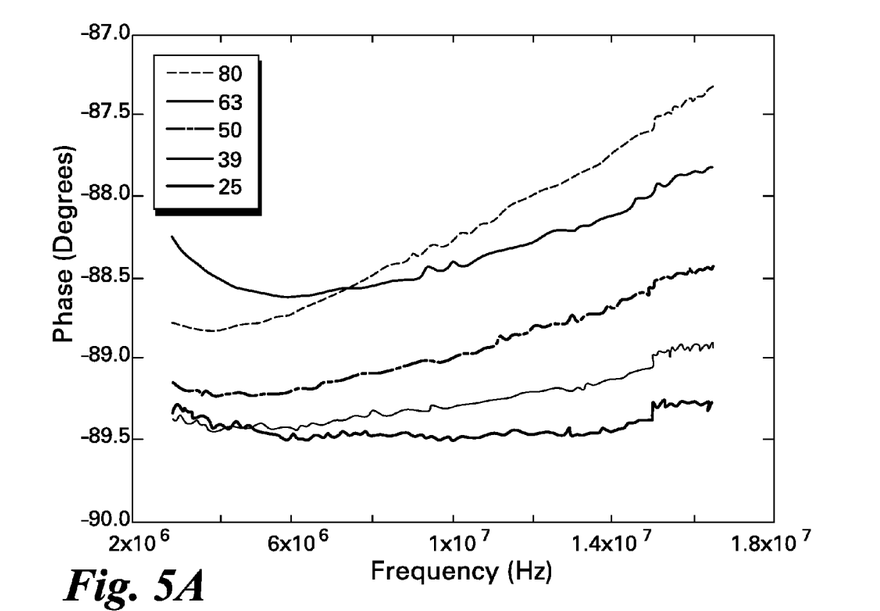
FIGS. 5A and 5B illustrate a comparison of conventional impedance spectroscopy and resonant RFID sensing in terms of phase shift (FIG. 5A) and frequency shift (FIG. 5B).
Figure 5B:
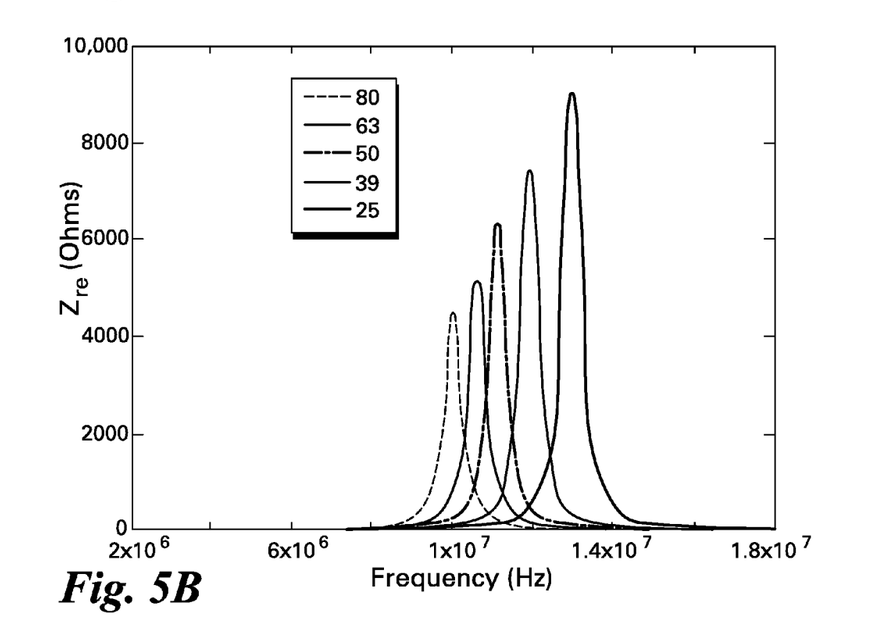
Figure 6A:
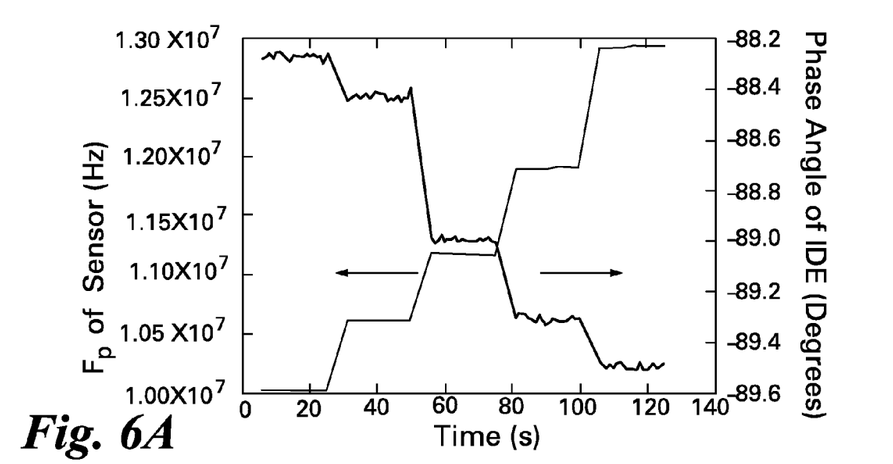
FIG. 6A illustrates a comparison of the relative noise in a measured signal of a sensor in accordance with one or more embodiments of the invention.
Figure 6B:
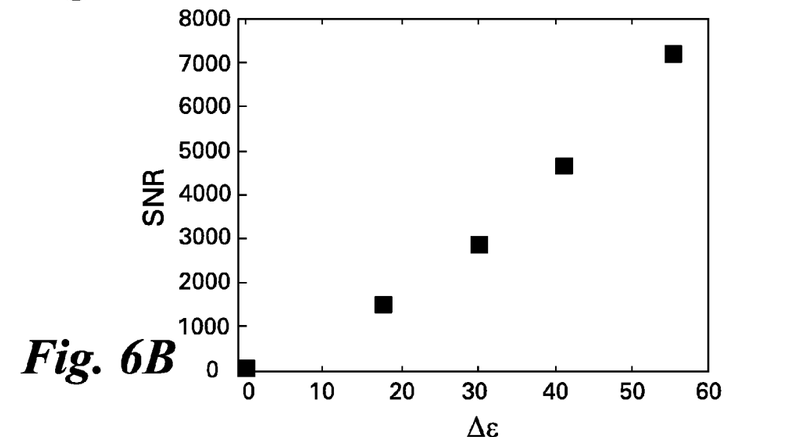
FIG. 6B illustrates a signal-to-noise ratio of sensor response measured using a resonant impedance sensor which may be used in accordance with one or more embodiments of the invention.
Figure 6C:
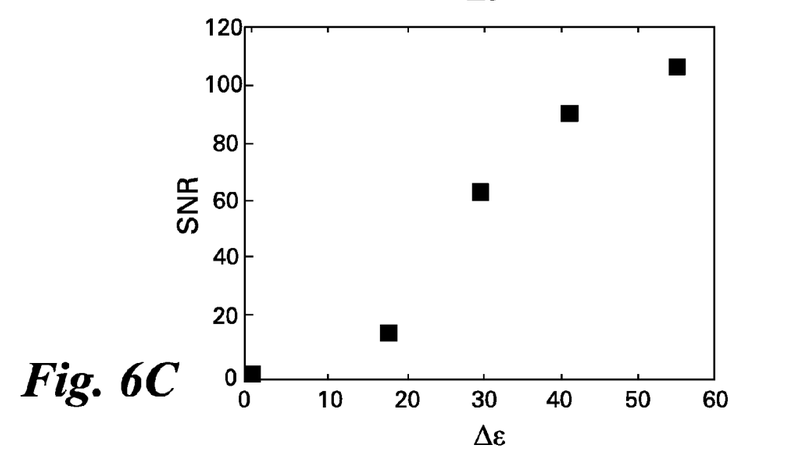
FIG. 6C illustrates a signal-to-noise ratio of sensor response measured using conventional impedance spectroscopy.

FIG. 5A illustrates experimental phase shift measurements from conventional impedance spectroscopy with solutions having dielectric constant ($\in$) ranging from about 25 to about 80. FIG. 5B illustrates results of validation experiments with solutions shown in FIG. 5A ($\in$=25-80) showing the phase shift measurements of an impedance spectrum and the peak shift of the resonance of the resonant impedance sensor. From the analysis of the collected data, it can be observed that conventional impedance spectroscopy measurements have a much larger relative noise in the signal than the resonant sensors used according to one or more embodiments of the present invention. To evaluate the signal-to-noise ratio (SNR) of a sensor response, data was processed as shown in FIGS. 6B and 6C. Compared to the conventional impedance spectroscopy (FIG. 6C), an embodiment of the resonant sensor provided an at least 100-fold enhancement in the SNR (FIG. 6B) over the smallest measured range of $\Delta\in$ with the corresponding improvement of detection limit of dielectric constant determinations. FIG. 6A shows raw data traces as liquids are flowed past the sensor for both sets of measurements (resonant and non-resonant).

Figure 7A:
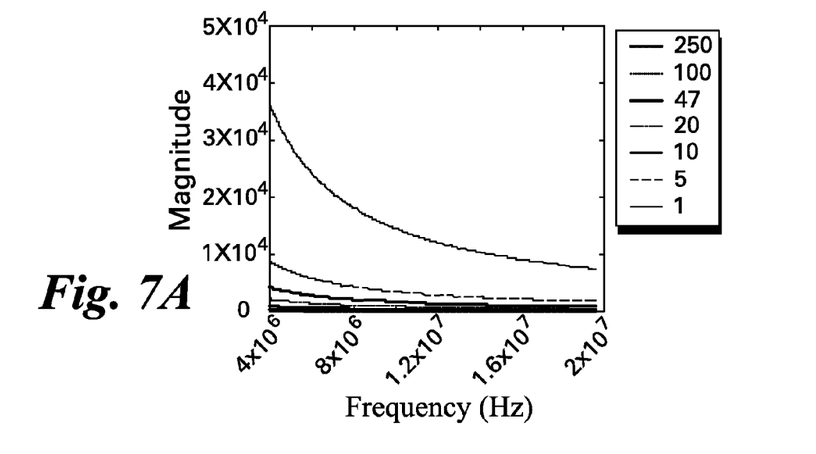
FIGS. 7A-7C illustrate complex impedance response to seven different capacitor values as magnitude (FIG. 7A), phase of non-resonant sensor versus frequency (FIG. 7B), and real impedance versus frequency of a resonant sensor (FIG. 7C).
Figure 7B:
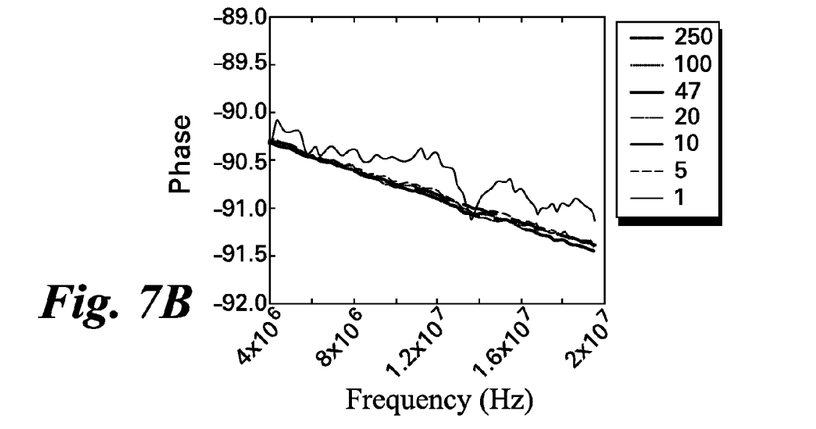
Figure 7C:
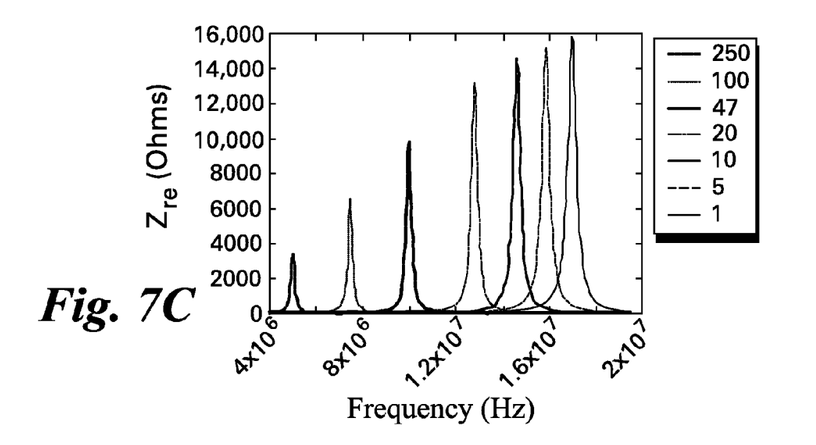

To compare performance of embodiments of the sensor with the ideal capacitance response, measurements were also taken in air with capacitors of different values (1 pF, 5 pF, 10 pF, 20 pF, 47 pF, 100 pF, and 250 pF) in both the non-resonant and resonant mode. Results are shown in FIGS. 7A-7C. The non-resonant response is shown as magnitude (FIG. 7A) and phase (FIG. 7B), and the resonant sensor response is shown as real impedance (FIG. 7C). In a strictly capacitance driven system, the response for phase (FIG. 7B) is relatively flat at 90 degrees and shows no correlation to capacitance.

Figure 8A:
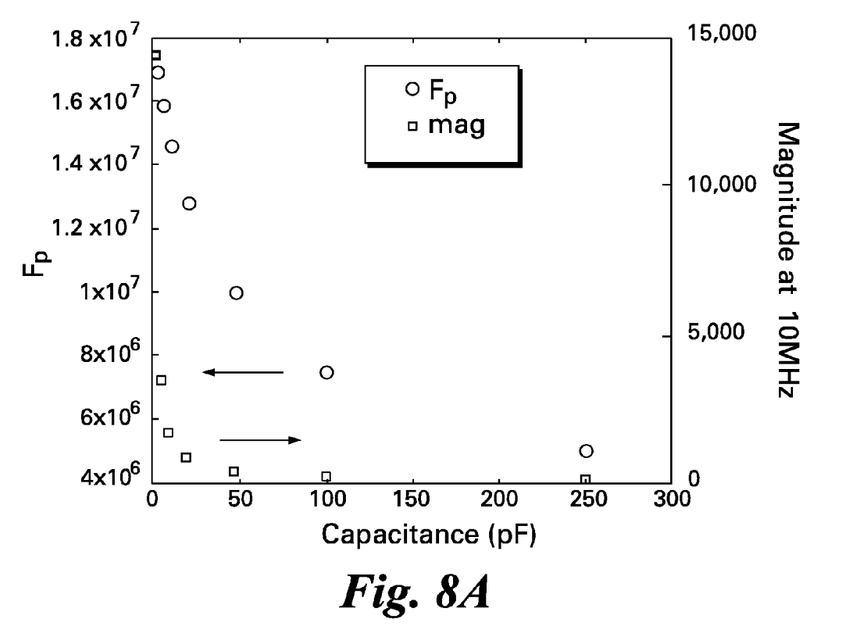
FIGS. 8A and 8B illustrate advantages of operating resonant impedance sensors relative to sensors used in conventional impedance spectroscopy by graphing a calibration curve of resonant frequency shifts versus capacitance constant in comparison to non-resonant magnitude (FIG. 8A) and by graphing a signal-to-noise ratio of resonant frequency shift as a function of change in dielectric constant compared to non-resonant magnitude (FIG. 8B).
Figure 8B:
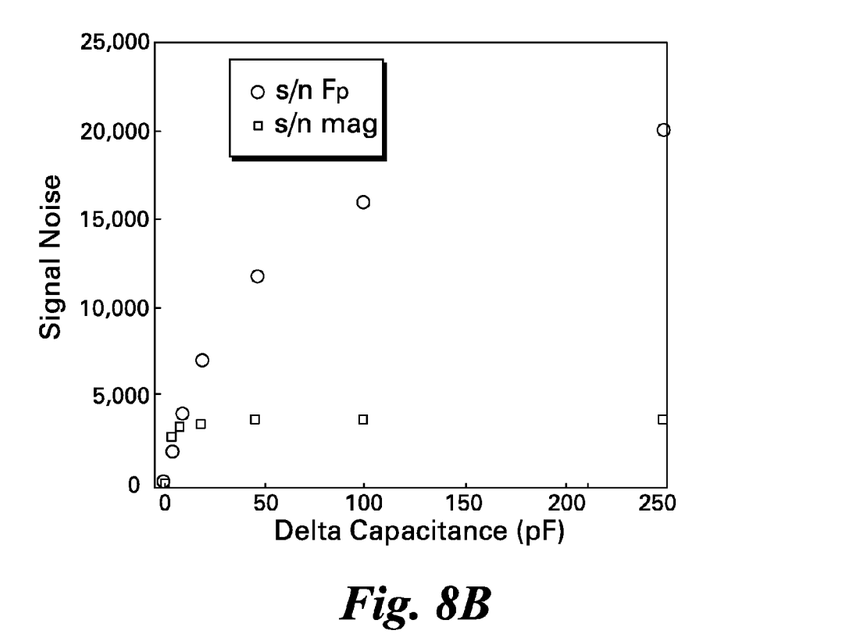

The responses of the non-resonant and resonant sensors as a function of capacitance are compared in FIGS. 8A and 8B. Because no correlation between response for phase and capacitance was seen (FIG. 7B), only magnitude was analyzed for the non-resonant sensor (FIG. 8A). The SNR comparison plotted in FIG. 8B shows that the resonant sensor has a significantly higher SNR than the non-resonant sensor.

As noted previously, one of the basic principles behind embodiments of the invention is that individual chemical will exhibit different dielectric properties and that those properties will vary in different ways in response to temperature changes. Embodiments of the invention incorporate techniques for exposing down-hole process fluid to varying temperatures, either by controlling the temperature manually or by taking advantage of natural temperature differences found in the drilling process. In one embodiment, different temperatures are induced in the measurement system flow cell by using known heating methods, including steady-state heating or dynamic heating. In one embodiment, different temperatures are provided from monitored natural temperature variations in different locations of the well bore. For example, in subsea drilling, the process fluid emerges from the core extremely hot (100° C.-200° C.). The process fluid cools as it rises in the pipes from the bottom of the sea because the ambient temperature of the subsea is very cold (5° C.-30° C.). This provides a natural temperature gradient as the process fluid is brought to the surface. In one embodiment, different temperatures are provided from monitored temperature variations in different special locations where temperatures are different.

In embodiments of the invention, resonant impedance spectroscopy, a direct measurement method that monitors basic physical properties of a process fluid, is utilized. Such a measurement method does not require the use of consumables such as carrier gases, reagents, or fluids. Further, such a measurement method does not require manual intervention. Also, such a measurement method does not require radioactive system components, as are required by many existing instruments and techniques used for down-hole measurements.

In embodiments of the invention, a flow cell is used for manual temperature control. In such embodiments, the measurements will be done in a slip stream. In embodiments of the invention, the need for optical fluid transparency is less important. In such embodiments, measurement techniques include techniques that do not require optical fluid transparency. Such techniques are less sensitive to surface fouling and do not require any windows. In embodiments of the invention, measurement techniques include techniques that provide different penetration depth of the signal into the fluid that is dependent on the design of the sensor transducer, such as, for example, the sensor coil. One way for decreasing sensor sensitivity to surface fouling is to increase signal penetration depth. Thus, the properties measured represent the bulk properties and surface fouling becomes insignificant. In one embodiment, such measurement techniques include designing a sensor transducer with sufficient penetration depth by maximizing the distance between electrodes or increasing the spacing and diameter of the sensing coil to provide insensitivity to fouling. In one embodiment, the method provided by the present invention comprises taking sensor readings with at least one resonant LCR sensor which is insensitive to sensor surface fouling.

In one embodiment, measurements of resonance impedance are performed by scanning frequencies across an expected region of resonance frequency of a LCR resonator. For example, if the LCR resonator has a resonance frequency Fp at about 10 MHz, then the measurements of resonance impedance of this resonator are performed by scanning frequencies from about 8 MHz to about 12 MHz.

In one embodiment, measurements of resonance impedance are performed by pulsed excitation of the LCR resonator followed by the recording of the ring-down pattern produced by the resonator response and taking the Fourier transform of the recorded pattern to compute the real and imaginary spectra. For example, if the LCR resonator has a resonance frequency Fp at about 10 MHz, then the measurements of resonance impedance of this resonator are performed by pulsing the resonator with a single pulse 0.1-10 ps pulse width or a sequence of pulses of 0.1-10 ps pulse width, recording the ring-down pattern produced by the resonator response and taking the Fourier transform of the recorded pattern to compute the real and imaginary spectra.

Figure 9:
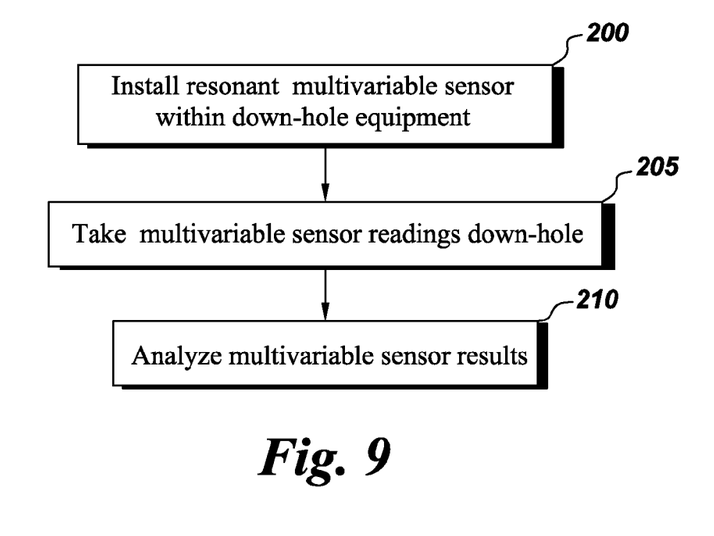
FIG. 9 illustrates process steps for detecting material properties of down-hole fluids in accordance with an embodiment of the invention.

With specific reference to FIG. 9, next will be described a method for detecting material properties of down-hole fluids in accordance with an embodiment of the invention. At Step 200, a resonant multivariable sensor is installed within down-hole equipment, which is then placed down-hole. The down-hole equipment may be logging equipment, such as, for example, a wireline logging assembly. Alternatively, the down-hole equipment may be drilling equipment used in the drilling and subsequent finishing of a well.

At Step 205, readings are taken down-hole with the resonant multivariable sensor. This Step 205 can be taken numerous times and at different environmental conditions. The different environmental conditions may include, for example, temperature and pressure. In other words, Step 205 can be taken at numerous different depths within the bore hole, either while the down-hole tool is moving or while it is stationary. The readings, or measurements, may be performed in multiphasic fluids found down-hole. Such multiphasic fluids may include, for example, gas, oil, water and sand. Finally, at Step 210, the results from the resonant multivariable sensor are analyzed.

In some embodiments, the multivariable sensor is an LCR sensor, a surface acoustic-wave sensor, a thickness shear mode sensor.

Figure 10:
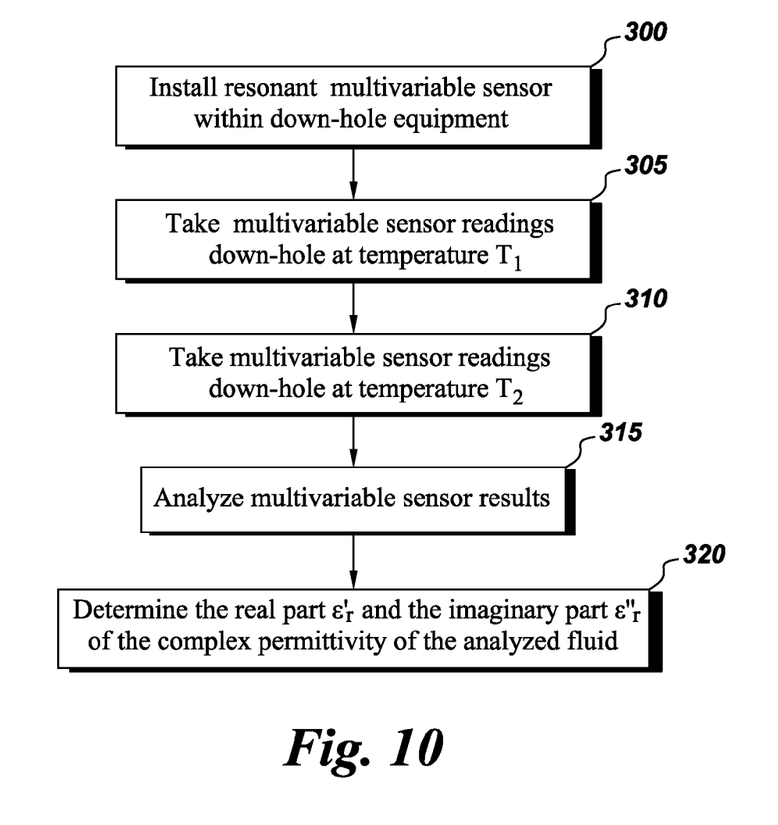
FIG. 10 illustrates process steps for detecting material properties of down-hole fluids at different temperatures in accordance with an embodiment of the invention.

With specific reference to FIG. 10, next will be described a method for detecting material properties of down-hole fluids in accordance with an embodiment of the invention utilizing the temperature-modulated spectral measurements of the sensor response. At Step 300, a resonant multivariable sensor is installed within down-hole equipment, which is then placed down-hole. The down-hole equipment may be logging equipment, such as, for example, a wireline logging assembly. Alternatively, the down-hole equipment may be drilling equipment used in the drilling and subsequent finishing of a well.

At step 305, sensor response is measured at one temperature T1 followed by the measurement of sensor response at second temperature T2 in step 310. Other additional temperatures can be also utilized for measurements of sensor response. Measurements at different temperatures provide the ability to measure the temperature-dependence of the complex permittivity ($\in'_r - j\in''_r$) of the monitored fluids and to correlate these changes with changes in the resonant impedance spectrum of the sensor (Step 315). In step 320, the real part $\in'_r$ of the complex permittivity of the monitored fluid is further calculated and the imaginary part $\in''_r$ of the complex permittivity of the monitored fluid is further calculated to provide the information on the nature of the measured fluid. In one embodiment, the method provided may be used to obtain sensor readings providing characteristics of a non-optically transparent fluid, for example, the water content (e.g. weight percent water) of a non-optically transparent crude oil-water mixture.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while embodiments have been described in terms that may initially connote singularity, it should be appreciated that multiple components may be utilized. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A down-hole monitoring system, comprising:
   down-hole equipment; and
   at least one resonant sensor for obtaining physical and chemical parameters of a down-hole fluid;
   wherein the resonant sensor comprises a single resonant inductor-capacitor-resistor (LCR) circuit and a sensing material disposed over a sensing region, wherein the sensing region comprises at least a portion of the single LCR circuit, and wherein temperature-dependent response coefficients of inductance L, capacitance C, and resistance R properties of the single LCR circuit and the sensing material are at least 5 percent different from one another, and wherein the difference in the temperature-dependent response coefficients of the properties of the single LCR circuit and sensing material enables the sensor to selectively detect one or more analytes sought to be detected in the down-hole fluid substantially independent of temperature.

2. The system of claim 1, wherein the down-hole equipment comprises a wireline logging assembly or drilling equipment.

3. The system of claim 1, wherein the sensor comprises a memory chip operable at one or more of a plurality of predetermined frequency ranges, forming a RFID sensor.

4. The system of claim 3, wherein the RFID sensor operates within a frequency range of from 1 kHz to 50,000 GHz, from 5 kHz to 500 GHz, or from 10 kHz to 50 GHz.

5. The system of claim 4, wherein the RFID sensor operates at a frequency of 125 kHz, a frequency of 134 kHz, or a frequency of 13.5 MHz.

6. The system of claim 1, wherein the sensor is configured to provide signals wired or wirelessly.

7. The system of claim 1, comprising a reader for reading signals from the sensor, wherein said reader is configured to read signals through a frequency sweep, a time-resolved sweep, or a ring-down detection.

8. The system of claim 1, wherein the sensor is configured to take measurements in a slip stream.

9. The system of claim 1, wherein the sensor comprises a sensor substrate and sensor electrodes in contact with a surface of the sensor substrate, wherein the sensor substrate and sensor electrodes have substantially different temperature response coefficients.

10. A method for detecting material properties of a down-hole fluid, comprising:
    placing at least one resonant sensor within down-hole equipment;
    taking sensor readings down-hole;
    transmitting the sensor readings to a reader device; and
    analyzing the sensor readings;
    wherein the resonant sensor comprises a single resonant inductor-capacitor-resistor (LCR) circuit and a sensing material disposed over a sensing region, wherein the sensing region comprises at least a portion of the single LCR circuit, and wherein temperature-dependent response coefficients of inductance L, capacitance C, and resistance R properties of the single LCR circuit and the sensing material are at least 5 percent different from one another, and wherein the difference in the temperature-dependent response coefficients of the properties of the single LCR circuit and sensing material enables the sensor to selectively detect one or more analytes sought to be detected in the down-hole fluid substantially independent of temperature.

11. The method of claim 10, wherein said placing comprises placing at least one resonant sensor within a wireline logging assembly or drilling equipment.

12. The method of claim 10, wherein the sensor provides a response to a temperature of a down-hole fluid in proximity to the sensor, wherein the response to the temperature is substantially independent of a response by the sensor to one or more chemical characteristics of the down-hole fluid in proximity to the sensor.

13. The method according to claim 12, wherein the sensor comprises a sensor substrate and sensor electrodes in contact with a surface of the sensor substrate, wherein the sensor substrate and sensor electrodes have substantially different temperature response coefficients.

14. The method of claim 10, wherein said transmitting comprises transmitting the sensor readings to a reader device configured to read signals through a frequency sweep, a time-resolved sweep, or a ring-down detection.

15. The method of claim 10, wherein said taking comprises taking sensor readings in a slip stream.

16. The method of claim 10, wherein said taking comprises taking sensor readings at different temperatures.

17. The method of claim 16, wherein said taking sensor readings at different temperatures comprises:
    inducing different temperatures within a flow cell through steady-state heating or dynamic heating; or taking sensor readings at different depths within a well bore.

18. The method of claim 10, wherein said taking comprises taking sensor readings without the use of consumables, manual intervention, or radioactive system components.

19. The method of claim 10, wherein said sensor readings provide characteristics of a non-optically transparent fluid.

20. The method of claim 10, wherein said taking comprises taking sensor readings with at least one resonant sensor insensitive to fouling.

21. A down-hole fluid monitoring system comprising:
down-hole equipment; and
at least one resonant sensor comprising a sensing film;
wherein the resonant sensor comprises a single resonant inductor-capacitor-resistor (LCR) circuit and the sensing film, the sensing film being disposed over a sensing region, wherein the sensing region comprises at least a portion of the single LCR circuit, and wherein temperature-dependent response coefficients of inductance L, capacitance C, and resistance R properties of the single LCR circuit and the sensing film are at least 5 percent different from one another, and wherein the difference in the temperature-dependent response coefficients of the properties of the single LCR circuit and sensing film enables the sensor to selectively detect one or more analytes sought to be detected in the down-hole fluid substantially independent of temperature.

22. The down-hole fluid monitoring system of claim 21 wherein the sensor comprises a sensor substrate selected from the group consisting of ceramics, glass, quartz, silicon, and organic polymers.

\* \* \* \* \*